US012521472B2

(12) United States Patent
Turner

(10) Patent No.: US 12,521,472 B2
(45) Date of Patent: *Jan. 13, 2026

(54) BREAST SHIELD WITH SUCKLING MOTION ONE WAY VALVE

(71) Applicant: Wayne D. Turner, Auburn, CA (US)

(72) Inventor: Wayne D. Turner, Auburn, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/233,811

(22) Filed: Aug. 14, 2023

(65) Prior Publication Data

US 2024/0058513 A1 Feb. 22, 2024

Related U.S. Application Data

(63) Continuation of application No. 18/187,531, filed on Mar. 21, 2023, now Pat. No. 11,759,554, which is a continuation-in-part of application No. 17/904,455, filed on Aug. 17, 2022, now Pat. No. 11,779,688.

(51) Int. Cl.

| | |
|---|---|
| ***A61M 1/06*** | (2006.01) |
| ***A61J 13/00*** | (2006.01) |
| ***A61M 39/24*** | (2006.01) |

(52) U.S. Cl.

CPC .............. *A61M 1/064* (2014.02); *A61J 13/00* (2013.01); *A61M 1/067* (2021.05); *A61M 1/06935* (2021.05); *A61M 39/24* (2013.01)

(58) Field of Classification Search

CPC ...... A61M 1/064; A61M 1/066; A61M 1/067; A61M 1/06; A61M 1/062; A61J 13/00

See application file for complete search history.

(56) References Cited

U.S. PATENT DOCUMENTS

| | | | | |
|---|---|---|---|---|
| 940,454 A * | 11/1909 | Fowler | A61M 1/064 | 604/75 |
| 1,113,942 A * | 10/1914 | Anderson | A01J 5/10 | 119/14.33 |
| 2,542,505 A * | 2/1951 | Gascoigne | A61M 1/06 | 119/14.41 |
| 4,311,141 A * | 1/1982 | Diamond | A61M 1/06 | 604/74 |
| 4,323,067 A * | 4/1982 | Adams | A61M 1/062 | 604/74 |
| 4,799,922 A * | 1/1989 | Beer | A61M 1/815 | 604/74 |
| 5,941,847 A * | 8/1999 | Huber | A61M 1/066 | 604/74 |
| 6,461,324 B1 * | 10/2002 | Schlensog | A61M 1/06 | 604/74 |
| 7,223,255 B2 * | 5/2007 | Myers | A61M 1/062 | 604/74 |
| 7,758,540 B2 * | 7/2010 | Yamashita | A61M 1/066 | 604/74 |

(Continued)

*Primary Examiner* — Scott J Medway

(74) *Attorney, Agent, or Firm* — PatentPC; Bao Tran

(57) ABSTRACT

The breast shield with suckling motion one-way valve of the present invention is a breast shield for use with a breast pump wherein the breast shield has a one-way valve configured to mimic the suckling action/motion of a nursing infant which can optionally be located beneath a plurality of holes to drain expressed milk. The breast shield of the present invention is used to improve the breast pumping experience, it can be used from any body position from sitting upright to laying fully recumbent, and it reduces or eliminates back flow of expressed milk.

20 Claims, 3 Drawing Sheets

(56) References Cited

U.S. PATENT DOCUMENTS

| | | | | |
|---|---|---|---|---|
| 7,824,363 | B2 * | 11/2010 | Myers | A61M 1/064 604/74 |
| 8,702,646 | B2 * | 4/2014 | Garbez | A61M 1/064 604/74 |
| 8,945,046 | B2 * | 2/2015 | Brittner | A61M 1/06 604/74 |
| 9,199,018 | B2 * | 12/2015 | Bauer | A61M 1/062 |
| 10,016,547 | B2 * | 7/2018 | Pollen | A61M 1/062 |
| 10,052,418 | B2 * | 8/2018 | Simmons | A61M 1/06 |
| 10,207,032 | B2 * | 2/2019 | Bauer | A61M 1/06 |
| 10,828,406 | B2 * | 11/2020 | Huang | A61M 1/06 |
| 11,298,445 | B2 * | 4/2022 | Analytis | A61M 1/06 |
| 11,413,381 | B2 * | 8/2022 | Quackenbush | A61M 1/066 |
| 11,541,156 | B2 * | 1/2023 | Hwang | A61M 1/067 |
| 2002/0183719 | A1 * | 12/2002 | Morton | A61B 5/6834 604/74 |
| 2008/0195039 | A1 * | 8/2008 | Kataoka | A61M 1/06 604/74 |
| 2008/0255503 | A1 * | 10/2008 | Quackenbush | A61M 1/064 604/74 |
| 2009/0062731 | A1 * | 3/2009 | Keyong | A61M 1/064 604/74 |
| 2010/0049122 | A1 * | 2/2010 | Jaeger-Waldau | A61M 1/815 604/74 |
| 2011/0071466 | A1 * | 3/2011 | Silver | A61M 1/064 604/74 |
| 2014/0128806 | A1 * | 5/2014 | Schlienger | A61M 1/067 604/74 |
| 2015/0065996 | A1 * | 3/2015 | Bartlett, II | A61M 1/062 604/74 |
| 2015/0148783 | A1 * | 5/2015 | Bartlett, II | A61M 1/062 604/74 |
| 2016/0296682 | A1 * | 10/2016 | Phillips | A61M 1/067 |
| 2017/0065753 | A1 * | 3/2017 | Nowroozi | A61M 1/06 |
| 2017/0095600 | A1 * | 4/2017 | Sherman | A61M 39/22 |
| 2018/0361040 | A1 * | 12/2018 | O'Toole | A61M 1/062 |
| 2021/0121614 | A1 * | 4/2021 | Schlienger | A61M 1/06 |

* cited by examiner

BREAST SHIELD WITH SUCKLING MOTION ONE WAY VALVE

CROSS-REFERENCE TO RELATED APPLICATIONS

This application claims benefit to the earlier filing date and right of priority under 35 U.S.C. § 120 to patent application Ser. No. 17/904,455, the contents of which are herein incorporated by reference under 37 CFR 1.57(b).

TECHNICAL FIELD OF THE INVENTION

This invention relates generally to a breast shield in the general form of a cone for the purpose of capturing milk expressed by a nursing woman from a breast while using a breast pump device connectively attached to either or both breasts of a nursing woman enabling a resting (for example in any recumbent, leaning, or sitting body position) use of said breast pump device.

This invention relates more specifically to a breast shield in the general form of a cone having a one-way valve for the purpose of capturing milk expressed by a nursing woman from a breast while using a breast pump device connectively attached to either or both breasts of a nursing woman enabling a resting use of said breast pump device.

This invention relates more specifically to a breast shield in the general form of a cone having a one-way valve configured to mimic a suckling action for the purpose of capturing milk expressed by a nursing woman from a breast while using a breast pump device connectively attached to either or both breasts of a nursing woman enabling a resting use of said breast pump device.

This invention relates generally to a breast shield in the general form of a cone having a plurality of milk drain holes positioned in side of said breast shield to enable a resting use of said breast pump by a nursing woman.

This invention relates more specifically to a breast shield in the general form of a cone having a plurality of milk drain holes positioned in side of said breast shield and a one-way flow valve to enable a back-flow restriction of expressed milk while in a resting use position of said breast pump by a nursing woman.

This invention relates more specifically to a breast shield in the general form of a cone having a plurality of milk drain holes positioned in side of said breast shield and a one-way valve for the purpose of capturing milk expressed by a nursing woman from a breast while using a breast pump device connectively attached to either or both breasts of a nursing woman enabling a resting use of said breast pump device.

This invention relates more specifically to a breast shield in the general form of a cone having a plurality of milk drain holes positioned in side of said breast shield and a one-way valve configured to mimic a suckling action for the purpose of capturing milk expressed by a nursing woman from a breast while using a breast pump device connectively attached to either or both breasts of a nursing woman enabling a resting use of said breast pump device.

BACKGROUND

There are available a plurality of breast shields in the general form of a cone for the purpose of capturing milk expressed by a nursing woman from a breast while using a breast pump device. These breast shields are designed for and enable a collection of expressed milk while the nursing woman is in a vertical or nearly vertical position.

Attempts to use the existing devices while in a resting position result in a mess of spilled milk and frustration. Use of a breast pump in a resting position is not practical given the current state of the art in breast shields.

There are available breast shields that have one-way valves. However, all existing breast shields suffer from the lack of a one-way valve configured to mimic the suckling action/motion of a nursing infant.

In light of the foregoing, there is a need for a breast shield with a plurality of holes to drain expressed milk for use by a nursing woman while in a resting position to capture and drain expressed milk down and away from the breast to enable a resting use by a nursing woman.

Importantly, in light of the foregoing, there is a need for a breast shield with a one-way valve configured to mimic the suckling action/motion of a nursing infant.

BRIEF SUMMARY OF THE INVENTION

The breast shield with suckling motion one-way valve of the present invention is a breast shield for use with a breast pump wherein the breast shield has a one-way valve configured to mimic the suckling action/motion of a nursing infant which can be located beneath a plurality of holes to drain expressed milk.

According to a first aspect of the invention, there is a suckling breast shield device comprising a breast receiving cone having a breast cup at a breast connection end opposite a narrowed neck flange, a funnel having a breast pump connection end (BPCE) opposite a narrowed neck flange connection end, and a one-way duckbill bi-valve (ODB) having a suckling action positioned between said narrowed neck flange and said breast pump connection end configured to prevent a back-flow.

According to a second aspect of the invention, there is a suckling breast shield device wherein said ODB comprises a soft-plastic material or a soft-rubber material.

According to a third aspect of the invention, there is a suckling breast shield device wherein said ODB further comprises an adjustment tab and an adjustable sleeve having an adjustment slot configured to reposition said ODB a distance from said narrowed neck flange.

According to a fourth aspect of the invention, there is a suckling breast shield device wherein said funnel further comprises a first milk drain hole, a second milk drain hole, and a stopper having a shield attachment end and a milk drain hole plug configured to enable a closing of either said first milk drain hole or said second milk drain hole.

According to a fifth aspect of the invention, there is a suckling breast shield device comprising a milk flow tube having a BPCE connection end opposite a milk container connection end, a cap, and a milk container, and optionally wherein said milk flow tube further comprises a one-way collection valve operatively attached to said milk container connection end.

According to a sixth aspect of the invention, there is a suckling breast shield device configured for a collection of an expressed milk.

According to a seventh aspect of the invention, there is a suckling breast shield device wherein a body of said ODB defines a bi-valve wedge-shaped body extending into said funnel, and/or wherein said body of said ODB defines a nipple-shaped body extending into said funnel, and/or wherein said body of said ODB is extending into said funnel and is configured to receive a breast nipple, and/or optionally wherein said body of said ODB is configured for axially centered placement of said breast nipple, and/or optionally configured for positioning said breast nipple inside said ODB.

According to an eighth aspect of the invention, there is a suckling breast shield device wherein a body of said ODB defines a triangular valve prism-shaped body extending into said funnel.

According to a ninth aspect of the invention, there is a suckling valve insert device for a breast shield comprising a one-way duckbill bi-valve (ODB) having a suckling action.

According to a tenth aspect of the invention, there is a suckling valve insert device wherein said ODB further comprises an adjustment tab and an adjustable sleeve having an adjustment slot configured to reposition said ODB.

According to an eleventh aspect of the invention, there is a suckling valve insert device wherein a body of said ODB defines a bi-valve wedge-shaped body, and/or wherein said body of said ODB defines a nipple-shaped body, and/or wherein said body of said ODB is configured to receive a breast nipple, and/or wherein said body of said ODB is configured to receive a breast nipple axially centered into said ODB, and/or configured for positioning said breast nipple inside said ODB.

According to a twelfth aspect of the invention, there is a suckling valve insert device wherein a body of said ODB defines a triangular valve prism-shaped body, and/or wherein said body of said ODB defines a nipple-shaped body, and/or wherein said body of said ODB is configured to receive a breast nipple, and/or wherein said body of said ODB is configured to receive said breast nipple axially centered into said ODB, and/or configured for positioning said breast nipple inside said ODB.

According to a thirteenth aspect of the invention, there is a suckling valve insert device further comprising a breast receiving cone having a breast cup at a breast connection end opposite a narrowed neck flange, and a funnel having a breast pump connection end opposite a narrowed neck flange connection end wherein said ODB is positioned between said narrowed neck flange and said breast pump connection end configured to prevent a back-flow.

An advantage of the present invention is that it incorporates a one-way valve configured to mimic the suckling action/motion of a nursing infant.

An advantage of the present invention is that a nursing woman can use a breast pump while in a resting position. A further advantage of the invention is that a nursing woman can use a breast pump while in a resting position and not spill or lose expressed milk, thereby eliminating the loss of milk and the resulting usual mess (spilled milk) associated with an attempt to use a breast pump while in a resting position.

An advantage of the present invention is that in mimicking an infants suckling action, said invention allows a nursing woman to enjoy a more enhanced and productive breast feeding experience when expressing milk.

The invention will now be described, by way of example only, with reference to the accompanying drawings in which:

DETAILED DESCRIPTION

Figure 1A:
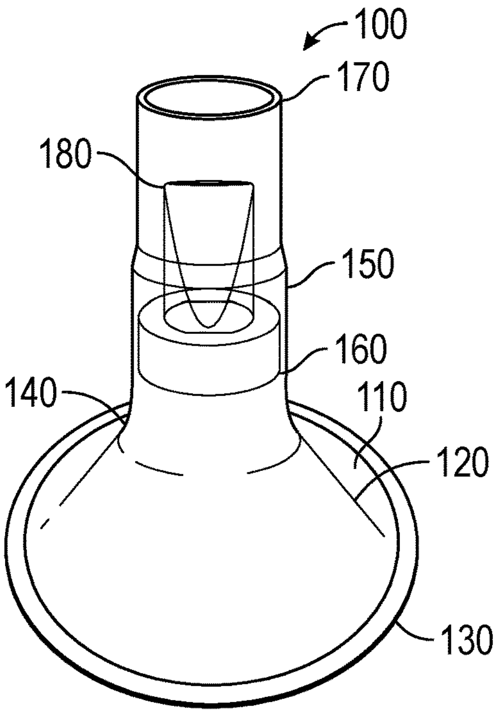
FIG. 1A is a perspective view of the breast shield with suckling motion one-way valve according to the invention.
Figure 1B:
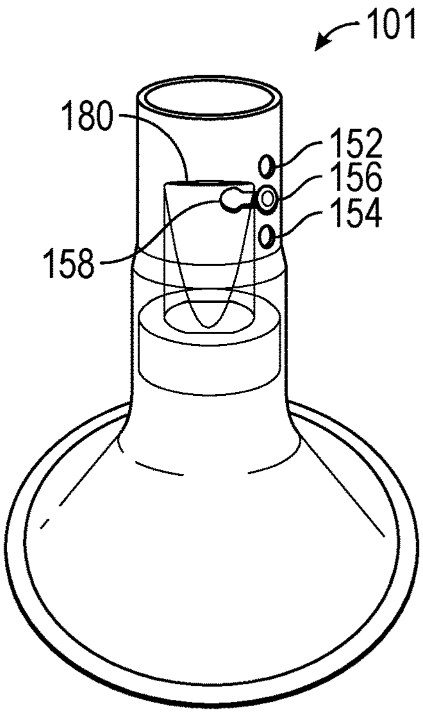
FIG. 1B is a perspective view of the breast shield with suckling motion one-way valve with milk drain holes according to the invention.
Figure 1C:
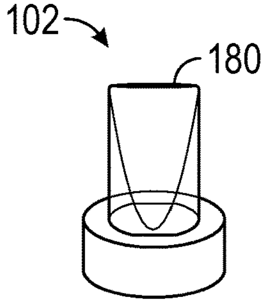
FIG. 1C is a perspective view of the suckling motion one-way valve insert according to the invention.
Figure 1D:
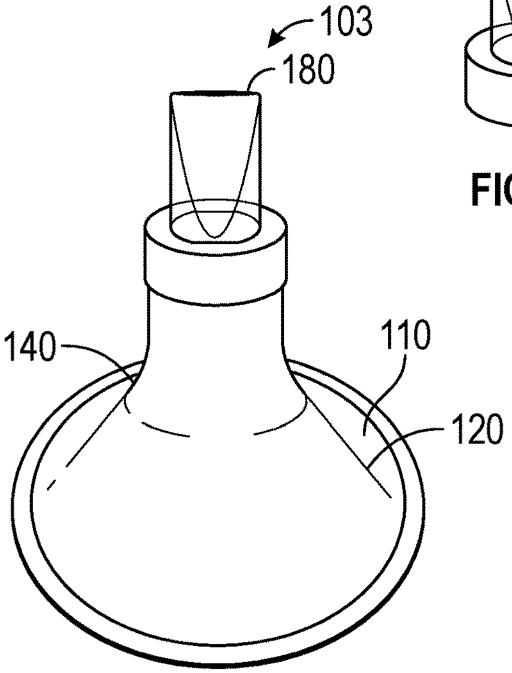
FIG. 1D is a perspective view of the breast shield with suckling motion one-way valve insert according to the invention.
Figure 1E:
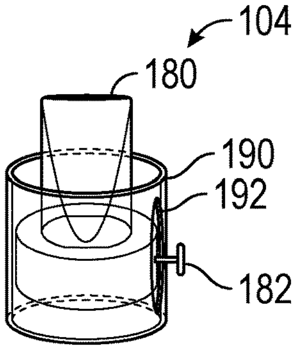
FIG. 1E is a perspective view of the breast shield with suckling motion one-way valve insert with an adjustable position means according to the invention.
Figure 2A:
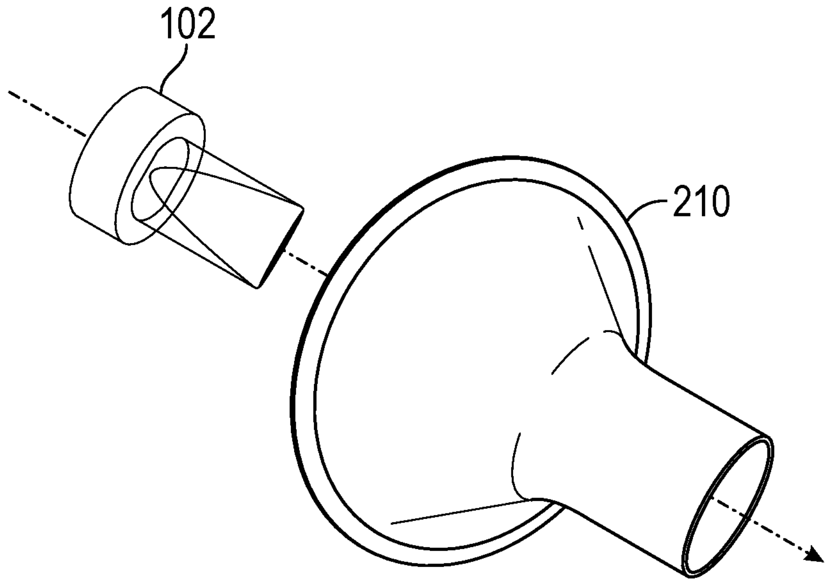
FIG. 2A is a perspective view of a breast shield with a suckling motion one-way valve insert according to the invention.
Figure 2B:
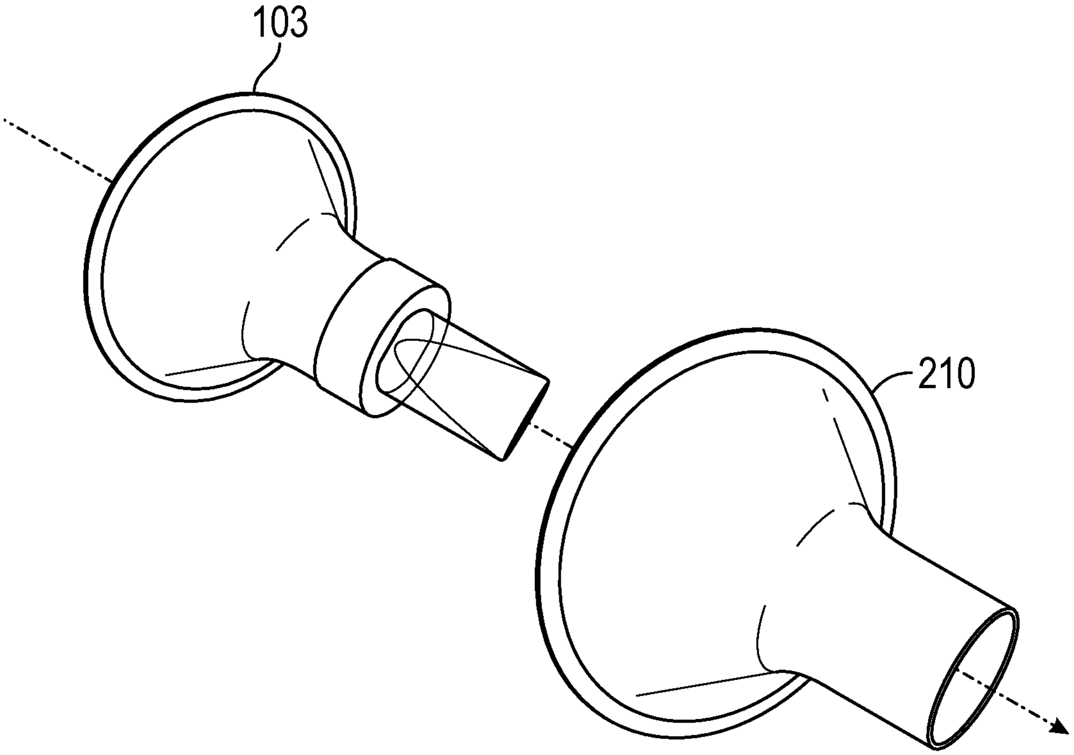
FIG. 2B is a perspective view of a breast shield with a breast shield with suckling motion one-way valve insert according to the invention.
Figure 3:
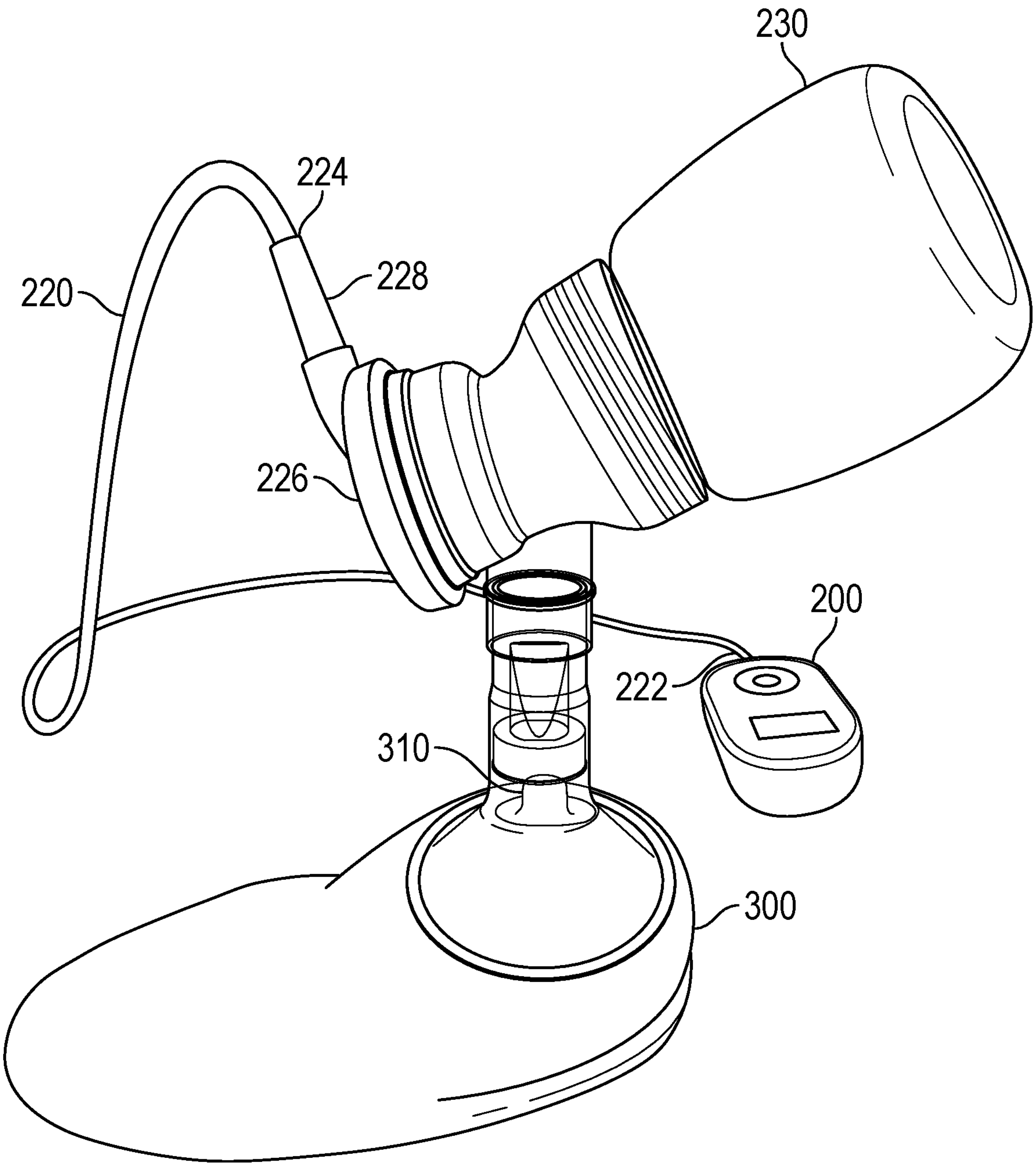
FIG. 3 is a perspective view of the breast shield with suckling motion one-way valve shown attached to an operational breast pump with milk container in a use position on top of a breast facing upwards for collection of expressed milk according to the invention.

The detailed embodiments of the present invention are disclosed herein. The disclosed embodiments are merely exemplary of the invention, which may be embodied in various forms. The details disclosed herein are not to be interpreted as limiting, but merely as the basis for the claims and as a basis for teaching one skilled in the art how to make and use the invention.

References in the specification to "one embodiment," "an embodiment," "an example embodiment," etcetera indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Furthermore, it should be understood that spatial descriptions (e.g., "above," "below," "up," "left," "right," "down," "top," "bottom," "vertical," "horizontal," etc.) used herein are for purposes of illustration only, and that practical implementations of the structures described herein can be spatially arranged in any orientation or manner.

The use of the term "recumbent" includes, but is not limited to the following: at least a person resting in a supine position or a person resting in a position laying, fully or partially on their back or side (left or right) with the front of their body in an upward or partially upward facing direction.

The use of the term/phrase "resting" or "resting position" includes, but is not limited to the following: the body of a person being in any recumbent, prone leaned (not completely vertical) back, prone leaned to the left body side, prone leaned to the right body side, or sitting vertical, sitting leaned back, sitting leaned to the left body side, or sitting leaned to the right side body position such that connective attachment of a breast shield to either or both a left breast and a right breast is possible for the purpose of expressing breast milk with the assistance/use of a breast pump to pump breast milk.

The use of the term/phrase "nursing woman" includes, but is not limited to the following: any person whose breasts are in a condition to lactate, a nursing mother (mom) breastfeeding a baby, and a nursing surrogate (maid) breastfeeding a baby.

The use of the term "suckling" includes, but is not limited to the following: mimicking an infants suckling action, in particular when nursing; and an action of the mouth as in the motion of an infants mouth when latched to a nipple wherein the lips, tongue, and jaw are moved in a sucking or chewing movement, in particular when nursing, which as a result triggers a breast to release a milk flow.

Index of Labelled Features in Figures (in numeric order): Referring to the Figures, there is shown the following elements/features.

Element 100 is a suckling breast shield device.

Element 101 is a suckling breast shield device with a first milk drain hole, a second milk drain hole, and a milk drain hole plug.

Element 102 is a suckling valve insert device for use in an existing breast shield.

Element 103 is a breast shield insert with suckling valve device for use in an existing breast shield.

Element 104 is an adjustable suckling valve insert device for use in an existing breast shield.

Element 110 is a breast receiving cone.

Element 120 is breast cup of a breast receiving cone (110).

Element 130 is breast connection end of a breast cup (120).

Element 140 is narrowed neck flange of a breast cup (120).

Element 150 is a funnel.

Element 152 is a first milk drain hole.

Element 154 is a second milk drain hole.

Element 156 is a stopper.

Element 158 is a shield attachment end of a stopped (156).

Element 160 is a breast pump connection end of a funnel (150).

Element 170 is a narrowed neck flange connection end of a funnel (150).

Element 180 is an one-way duckbill bi-valve (ODB) having a suckling action.

Element 182 is an adjustment tab for and ODB 180.

Element 190 is an adjustable sleeve for repositioning an ODB (180).

Element 192 is an adjustment slot.

Element 200 is a breast pump.

Element 210 is a breast shield for use with a breast pump (200).

Element 220 is a milk tube.

Element 222 is a breast pump connection end (BPCE) connection end of a milk tube (220).

Element 224 is a milk container connection end of a milk tube (220).

Element 226 is a cap.

Element 228 is a one-way collection valve.

Element 230 is a milk container.

Element 300 is a breast.

Element 310 is a breast nipple.

In an embodiment the breast shield of the present invention features a one-way flow valve having a plurality of flaps configured in a two or three leafed valve. The breast shield of the present invention features a duck-bill two sided valve configured with rounded square shaped edges as shown in the figures. In this configuration the two sides of the valve expand away from each other forming a shape similar to the shape formed by the mouth of a suckling infant.

In an embodiment the breast shield of the present invention features a one-way flow valve positioned covering the interior of the funnel so as to enable expressed milk back flow prevention thereby reducing loss of expressed milk and keeping the breast free of accumulated expressed milk. The one-way flow valve thus helps ensure a comfortable and complete expression without the breast becoming wet/saturated with expressed milk.

In an embodiment the breast shield of the present invention features an adjustable range of milk drain holes for milk exiting to accommodate differences in the length of the nipple. The milk drain holes could alternatively be placed in different locations, and/or increased in number to facilitate a plurality of different models with finer and finer degrees of precision as to suitability for specific nipple lengths. The milk drain holes may alternatively be reduced to a single hole without an accompanying stopper.

In all embodiments, the breast receiving cone can be made from a material that is food grade, sterilizable, washable, and reusable. The one-way flow valve is made from a material that is soft feeling to the sense of touch, food grade, sterilizable, washable, reusable and moves easily and readily to enable opening the one-way flow valve flaps when the one-way flow valve is placed into the inside of the funnel of the breast receiving cone thereby creating the breast receiving cone with one-way flow valve positioned to enable a back flow prevention. The one-way flow valve is positioned above a narrowed neck flange and below the milk drain holes.

In alternate embodiments, the one-way flow valve is an external device/apparatus that is positioned in, and or connectively attached to a tube and one or both of the milk drain holes to enable a back flow prevention of expressed milk once drawn past said once-way flow valve.

In an embodiment the breast shield of the present invention features milk drain ports "close off capability of all drain holes" to allow traditional breast pump container fill with woman sitting up.

In an embodiment the breast shield of the present invention features breast shield materials to include medical grade hard plastic, soft silicone rubber, etc;

In an embodiment the breast shield of the present invention features a vacuum pump sucking capability to milk container line end to draw milk out of tubing line.

In an embodiment the breast shield of the present invention features a configuration to allow woman to breast pump in any position to include upright, side lying, or relaxed position.

In an embodiment the breast shield of the present invention features a one way valve on end connectively attached to the exit end that connects to the breast pump.

The breast shield of the present invention can be configured to reduce and/or prevent spillage of woman's expressed milk during pumping phase in that the expressed milk exits breast nipple and follows a short (shallow) centrally guided path through the one way valve for said expressed milk to drain through milk line into container.

In an embodiment, the breast shield of the present invention is combined with a tube to connect either milk drain hole to a container to enable capture of expressed milk while using the breast receiving cone with a breast pump attached to the breast pump connection end. Expressed milk flows out of the breast shield of the present invention and through the connectively attached milk drain hole connection of the tube, through the tube and out the open end of the tube. When the tube is inserted through the cap the expressed milk can be collected directly into a container which the cap is connectively attached to.

In an embodiment, a nursing woman (mom) will utilize two breast shields to enable pumping from both breasts for milk to be expressed (pumped) at the same time. The present invention allows for one or two breasts to pump on the side lying, reclining and supine positions.

The present invention makes it easier and more comfortable to hold the breast shield in the correct (shield centered around the nipple) position since the woman's arm is resting on the arm of the chair or on the bed if she is not using a hands free pumping bra. It is noted that use of/with a hands free pumping bra to assist in holding the breast shield in the correct nipple centered in the opening position will prevent nipple tissue damage and reduce neck, shoulder and back fatigue and strain by avoiding the need to lean forward when pumping in upright position.

In one embodiment of the invention, there is a breast shield for a resting position use by a nursing woman to capture an expressed milk while using a breast pump comprising a breast receiving cone having a "breast cup" at a breast connection end, a narrowed neck flange, a funnel, and a breast pump connection end at an opposite end of said breast receiving cone comprising a first milk drain hole, a second milk drain hole, and a stopper having a shield attachment end and a milk drain hole plug configured to enable a closing of either said first milk drain hole or said second milk drain hole thereby enabling said nursing woman to use said breast pump to capture said expressed milk while said nursing woman is in said resting position.

In an embodiment of the invention, there is a breast shield for a resting position use by a nursing woman to capture an expressed milk while using a breast pump comprising a breast receiving cone having a breast cup at a breast connection end, a narrowed neck flange, a funnel, and a breast pump connection end at an opposite end of said breast receiving cone comprising a first milk drain hole, a second milk drain hole, and a stopper having a shield attachment end and a milk drain hole plug configured to enable a closing of either said first milk drain hole or said second milk drain hole thereby enabling said nursing woman to use said breast pump to capture said expressed milk while said nursing woman is in said resting position, wherein said breast receiving cone is further comprises a one-way flow valve for preventing a back-flow of said expressed milk connectively attached to and completely closing said breast receiving cone between said narrowed neck funnel and said breast pump connection end enabling the prevention of said back-flow of said expressed milk while said nursing woman is in said resting position.

In use, the breast breast shield of the present invention is connected to a breast pump and the breast pump is turned on to enable pumping/suction to cause milk to be expressed.

To begin using a preferred embodiment having milk drain holes, one of the milk drain holes is closed/stopped with the milk drain hole plug of the stopper (not separately numbered) by rotating the stopper into position above the milk drain hole to be closed (not available for use) and inserting the milk drain hole plug into the milk drain hole thereby closing it. The expressed milk will flow out of the funnel and through the milk drain hole. The expressed milk will flow out of the funnel and pass through the flaps of the one-way flow valve and then out through the milk drain hole where the embodiment of the invention has the one-way flow valve included.

Use of the invention is simple. A breast is inserted into the breast connection end of the breast receiving cone. The breast is best positioned such that the nipple is directed pointing upward into the center of the narrowed neck flange. This enables expressed milk to be safely drawn up past the one-way flow valve through the flaps where the embodiment includes the one-way flow valve. The centered position not only enhances comfort but also ensures that the milk drain hole that is left open is positioned to enable flow of the expressed milk out of the device without impedance.

In any embodiment, the breast receiving cone is commonly known to the general breast pump using/aware public as a "breast shield." In any embodiment wherein a container is used to collect expressed milk, said container comprises any of the following: a container, a milk bottle, a nursing bottle, a baby bottle, a bag, a milk bag, a nursing bottle bag, a baby bottle bag, a pitcher and/or a cup.

In a preferred embodiment of the present invention, there is a suckling breast shield device comprising a breast receiving cone having a breast cup at a breast connection end opposite a narrowed neck flange, a funnel having a breast pump connection end (BPCE) opposite a narrowed neck flange connection end, and a one-way duckbill bi-valve (ODB) having a suckling action positioned between said narrowed neck flange and said breast pump connection end configured to prevent a back-flow.

In an alternate embodiment of the present invention, there is a suckling breast shield device wherein said ODB comprises a soft-plastic material or a soft-rubber material.

In an alternate embodiment of the present invention, there is a suckling breast shield device wherein said ODB further comprises an adjustment tab and an adjustable sleeve having an adjustment slot configured to reposition said ODB a distance from said narrowed neck flange.

In an alternate embodiment of the present invention, there is a suckling breast shield device wherein said funnel further comprises a first milk drain hole, a second milk drain hole, and a stopper having a shield attachment end and a milk drain hole plug configured to enable a closing of either said first milk drain hole or said second milk drain hole.

In an alternate embodiment of the present invention, there is a suckling breast shield device further comprising a milk flow tube having a BPCE connection end opposite a milk container connection end, a cap, and a milk container.

In an alternate embodiment of the present invention, there is a suckling breast shield device wherein said milk flow tube further comprises a one-way collection valve operatively attached to said milk container connection end.

In an alternate embodiment of the present invention, there is a suckling breast shield device configured for a collection of an expressed milk.

In an alternate embodiment of the present invention, there is a suckling breast shield device wherein a body of said ODB defines a bi-valve wedge-shaped body extending into said funnel.

In an alternate embodiment of the present invention, there is a suckling breast shield device wherein said body of said ODB defines a nipple-shaped body extending into said funnel.

In an alternate embodiment of the present invention, there is a suckling breast shield device wherein said body of said ODB is extending into said funnel and is configured to receive a breast nipple.

In an alternate embodiment of the present invention, there is a suckling breast shield device wherein said body of said ODB is configured for axially centered placement of said breast nipple.

In an alternate embodiment of the present invention, there is a suckling breast shield device configured for positioning said breast nipple inside said ODB.

In an alternate embodiment of the present invention, there is a suckling breast shield device wherein a body of said ODB defines a triangular valve prism-shaped body extending into said funnel.

In an alternate embodiment of the present invention, there is a suckling breast shield device wherein said body of said ODB defines a nipple-shaped body extending into said funnel.

In an alternate embodiment of the present invention, there is a suckling breast shield device wherein said body of said ODB is extending into said funnel configured to receive a breast nipple.

In an alternate embodiment of the present invention, there is a suckling breast shield device wherein said body of said ODB is configured for axially centered placement of said breast nipple.

In an alternate embodiment of the present invention, there is a suckling breast shield device configured for positioning said breast nipple inside said ODB.

In a preferred embodiment of the present invention, there is a suckling valve insert device for a breast shield comprising a one-way duckbill bi-valve (ODB) having a suckling action.

In an alternate embodiment of the present invention, there is a suckling valve insert device for a breast shield wherein said ODB comprises a soft-plastic material or a soft-rubber material.

In an alternate embodiment of the present invention, there is a suckling valve insert device for a breast shield wherein said ODB further comprises an adjustment tab and an adjustable sleeve having an adjustment slot configured to reposition said ODB.

In an alternate embodiment of the present invention, there is a suckling valve insert device for a breast shield wherein a body of said ODB defines a bi-valve wedge-shaped body.

In an alternate embodiment of the present invention, there is a suckling valve insert device for a breast shield wherein said body of said ODB defines a nipple-shaped body.

In an alternate embodiment of the present invention, there is a suckling valve insert device for a breast shield wherein said body of said ODB is configured to receive a breast nipple.

In an alternate embodiment of the present invention, there is a suckling valve insert device for a breast shield wherein said body of said ODB is configured to receive a breast nipple axially centered into said ODB.

In an alternate embodiment of the present invention, there is a suckling valve insert device for a breast shield configured for positioning said breast nipple inside said ODB.

In an alternate embodiment of the present invention, there is a suckling valve insert device for a breast shield wherein a body of said ODB defines a triangular valve prism-shaped body.

In an alternate embodiment of the present invention, there is a suckling valve insert device for a breast shield wherein said body of said ODB defines a nipple-shaped body.

In an alternate embodiment of the present invention, there is a suckling valve insert device for a breast shield 6 wherein said body of said ODB is configured to receive a breast nipple.

In an alternate embodiment of the present invention, there is a suckling valve insert device for a breast shield wherein said body of said ODB is configured to receive said breast nipple axially centered into said ODB.

In an alternate embodiment of the present invention, there is a suckling valve insert device for a breast shield configured for positioning said breast nipple inside said ODB.

In an alternate embodiment of the present invention, there is a suckling valve insert device for a breast shield further comprising a breast receiving cone having a breast cup at a breast connection end opposite a narrowed neck flange, and a funnel having a breast pump connection end opposite a narrowed neck flange connection end wherein said ODB is positioned between said narrowed neck flange and said breast pump connection end configured to prevent a backflow.

An advantage of the present invention is that a one-way valve configured to mimic the suckling action/motion of a nursing infant is centered in the breast shield improving the use of a breast pump and offering a more natural nursing motion to the breast pumping experience.

An advantage of the present invention is that a nursing woman with one or more injured, sore, raw, bitten, or sensitive nipples can use a breast pump while in a resting or sitting position.

An advantage of using the present invention is that it allows a nursing woman to pump (i.e. use a breast pump to express milk) in a reclined position even if she is unable to tolerate sitting up to pump due to physical and/or medical condition, i.e. headache, hemorrhoids, dizziness, (any condition which would not allow her to tolerate sitting up to pump).

An advantage of the present invention is that said nursing woman with nipple injury or soreness can use a breast pump while in a resting position or sitting position and not spill or lose expressed milk, thereby eliminating lost milk and the resulting usual mess (spilled milk) associated with an attempt to use a breast pump while in a recumbent or sitting position.

An advantage of the present invention is that the said one way valve is that it more effectively targets the end center portion of the breast nipple promoting maximum concentrated infant suckling milk expression.

An advantage of the present invention is that the one way valve helps curb chafing, excessive rubbing against wall flange to surrounding area of nipple preventing injuries to breast.

An advantage of the present invention is that in mimicking an infants suckling action, said invention allows a nursing woman to enjoy a more enhanced and productive breast feeding experience when expressing milk. Several key aspects are as follows: 1) Increases stimulation and lengthens the center positioned breast nipple, therein extending said nipple length within close proximity and into the opening of suckling motion one way valve, thereby supporting and improving the triggering of the milk ejection reflex (MER); 2) Steadily holds the breast nipple in a centered position and maintains an optimal close-to-zero air measurement in the cavity area between the nipple/areola and suckling motion one way valve; and 3) Allows for an adjustment in maintaining a continual steady baseline, low level vacuum in order to maintain a continuous air-seal on the nipple/areola area of the breast during breast pumping.

The invention has been described by way of examples only. Therefore, the foregoing is considered as illustrative only of the principles of the invention. Further, since numerous modifications and changes will readily occur to those skilled in the art, it is not desired to limit the invention to the exact construction and operation shown and described, and accordingly, all suit-able modifications and equivalents may be resorted to, falling within the scope of the claims.

Although the invention has been explained in relation to various embodiments, it is to be understood that many other possible modifications and variations can be made without departing from the spirit and scope of the invention.

The invention claimed is:

1. A breast shield device configured to collect expressed milk, comprising:

a breast receiving cone having a breast cup at a breast connection end, a narrowed neck flange coupled to the breast cup, a funnel having a narrowed neck flange connection end coupled to the narrowed neck flange, a first breast pump connection end opposite the narrowed neck flange, and a longitudinal axis;

a one-way repositioning duckbill bi-valve positioned between the narrowed neck flange and the breast pump connection end and configured to prevent a back-flow and to mimic a suckling action;

wherein the one-way duckbill bi-valve is adjustable, relative to the narrowed neck flange, along the longitudinal axis of the funnel, wherein the one-way duckbill bi-valve defines a nipple-shaped body extending into the funnel and the body of the one-way duckbill bi-valve is configured to receive a breast nipple.

2. The breast shield device of claim 1, comprising a breast shield insert, wherein the one-way duckbill bi-valve comprises a soft plastic material or a soft rubber material.

3. The breast shield device of claim 1, wherein the funnel further comprises:

a first milk drain hole, a second milk drain hole, and a stopper comprising a shield attachment end and a milk drain hole plug configured to enable a closing of either the first milk drain hole or the second milk drain hole.

4. The breast shield device of claim 1, further comprising:

a milk flow tube having a second breast pump connection end and a milk container connection end opposite the second breast pump connection end;

a cap; and a milk container.

5. The breast shield device of claim 4, wherein the milk flow tube further comprises a one-way collection valve operatively attached to the milk container connection end.

6. The breast shield device of claim 1, wherein the one-way duckbill bi-valve defines a wedge-shaped body that extends through the funnel or a triangular prism-shaped body extending into the funnel.

7. The breast shield device of claim 1, wherein the one-way duckbill bi-valve is axially centered.

8. The breast shield device of claim 1, wherein the breast shield device allows the breast nipple to be positioned inside the one-way duckbill bi-valve.

9. The breast shield device of claim 1, wherein the one-way duckbill bi-valve defines a nipple-shaped body extending into the funnel.

10. The breast shield device of claim 1, wherein the body of the one-way duckbill bi-valve is configured for axially centered placement of the breast nipple.

11. A method of collecting expressed milk, the method comprising:

providing a breast shield device comprising:

a breast receiving cone having a breast cup at a breast connection end, a narrowed neck flange coupled to the breast cup, a funnel having a narrowed neck flange connection end coupled to the narrowed neck flange, a first breast pump connection end opposite the narrowed neck flange, and a longitudinal axis;

a repositionable one-way duckbill bi-valve configured to mimic a suckling action, wherein the one-way duckbill bi-valve is moveable, relative to the narrowed neck flange, along the longitudinal axis of the funnel, wherein the one-way duckbill bi-valve defines a nipple-shaped body extending into the funnel and is configured to receive a breast nipple; and collecting expressed milk from the breast shield device in a resting position.

12. The method of claim 11, comprising:

providing a breast cup at the breast connection end, the breast connection end being opposite the narrowed neck flange, and wherein the one-way duckbill bi-valve is positioned between the narrowed neck flange and the breast pump connection end.

13. The method of claim 11, wherein a body of the one-way duckbill bi-valve defines a triangular valve prism-shaped body.

14. The method of claim 11, comprising providing a milk flow tube in the form of a one-way collection valve operatively attached to a milk container connection end.

15. The method of claim 11, wherein a body of the one-way duckbill bi-valve defines a triangular valve prism-shaped body extending into said funnel.

16. The method of claim 11, comprising axially centering a said breast nipple in the one-way duckbill bi-valve.

17. The method of claim 11, comprising positioning said breast nipple inside the one-way duckbill bi-valve.

18. The method of claim 11, wherein a body of the one-way duckbill bi-valve defines a bi-valve wedge-shaped body.

19. The method of claim 11, comprising receiving said breast nipple into a center of the one-way duckbill bi-valve.

20. The method of claim 11, comprising providing a milk flow tube having a second breast pump connection end and a milk container connection end opposite the second breast pump connection end; a cap; and a milk container.

* * * * *